US009822143B2

(12) United States Patent
Sun et al.

(10) Patent No.: US 9,822,143 B2
(45) Date of Patent: *Nov. 21, 2017

(54) REMOVAL OF HIGH MOLECULAR WEIGHT AGGREGATES USING HYDROXYAPATITE CHROMATOGRAPHY

(71) Applicant: Wyeth LLC, Madison, NJ (US)

(72) Inventors: Shujun Sun, Brentwood, NH (US); Christopher Gallo, Windham, NH (US); Brian Kelley, Medford, MA (US)

(73) Assignee: Wyeth LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/803,071

(22) Filed: Mar. 14, 2013

(65) Prior Publication Data
US 2013/0197198 A1   Aug. 1, 2013

Related U.S. Application Data

(63) Continuation of application No. 10/958,595, filed on Oct. 6, 2004.

(60) Provisional application No. 60/514,018, filed on Oct. 27, 2003, provisional application No. 60/523,335, filed on Nov. 20, 2003.

(51) Int. Cl.
| C07K 16/28 | (2006.01) |
| C07K 1/16 | (2006.01) |
| B01D 15/36 | (2006.01) |
| B01D 15/38 | (2006.01) |
| B01J 20/04 | (2006.01) |
| B01J 20/282 | (2006.01) |
| C07K 16/06 | (2006.01) |
| C07K 16/22 | (2006.01) |
| C07K 16/18 | (2006.01) |
| C07K 16/24 | (2006.01) |

(52) U.S. Cl.
CPC ............. *C07K 1/165* (2013.01); *B01D 15/36* (2013.01); *B01D 15/3804* (2013.01); *B01D 15/3847* (2013.01); *B01J 20/048* (2013.01); *B01J 20/282* (2013.01); *C07K 16/065* (2013.01); *C07K 16/18* (2013.01); *C07K 16/22* (2013.01); *C07K 16/24* (2013.01); *C07K 16/2851* (2013.01); *B01D 15/361* (2013.01); *B01D 15/3809* (2013.01)

(58) Field of Classification Search
None
See application file for complete search history.

(56) References Cited

U.S. PATENT DOCUMENTS

| 5,633,162 A | 5/1997 | Keen et al. |
| 7,122,641 B2 | 10/2006 | Vedantham et al. |
| 9,469,672 B2 * | 10/2016 | Sun ........................ B01D 15/36 |
| 2003/0165496 A1 | 9/2003 | Basi et al. |
| 2003/0166869 A1 * | 9/2003 | Vedantham ............... C07K 1/16 |
| | | 530/387.1 |

FOREIGN PATENT DOCUMENTS

| WO | 03/059935 | 7/2003 |
| WO | 2004076485 | 9/2004 |

OTHER PUBLICATIONS

Coppola et al., "High-Performance Liquid Chromatography of Amino Acids, Peptides and Proteins: XCIII. Comparison of Methods for the Purification of Mouse Monoclonal Immunoglobulin M Autoantibodies," Journal of Chromatography 476:269-290 (1989).
Franklin, S., "Removal of Aggregate from an IgG4 Product Using CHT™ Ceramic Hydroxyapatite," Chromatography Tech Note 2940, Bio-Rad Laboratories, Inc. (2002).
Gagnon, Purification Tools for Monoclonal Antibodies, 1996, Validated Biosystems, Chapter 5, p. 87-102.
Giovannini et al., "Comparison of Different Types of Ceramic Hydroxyapatite for the ChromatographiC Separation of Plasmid DNA and a Recombinant Anti-Rhesus D Antibody," Bioseparation 9:359-368 (2001).
Giovannini et al., "Isolation of a Recombinant Antibody from Cell Culture Supernatant: Continuous Annular Versus Batch and Expanded-Bed Chromatography," Biotechnology and Bioengineering 73(6):522-529 (2001).
Josic, D and Lim, Y.-P., "Analytical and Preparative Methods for Purification of Antibodies," Food Technol. Biotechnol., 39(3):215-226 (2001).
Jungbauer et al., "Comparison of Protein A, Protein G and Copolymerized Hydroxyapatite for the Purification of Human Monoclonal Antibodies," Journal of Chromatography 476:257-268 (1989).
Karlsson et al., "Ion Exchange Chromatography," In: Protein Purification (VCH Publishers, Inc., New York, NY) pp. 107-148 (1989).
Kennedy, Current Protocols in Protein Sciences, 1995, 8.4.1-8.4.21.
Lullau et al., "Development of a Bioprocess for Murine Dimeric IgA Production," Biotechnology Techniques 12(6):425-430 (1998).
Ogawa et al. "Effect of pH on Gradient Elution of Different Proteins on Two Types of Ceramic Hydroxyapatite," American Laboratory 171-17K (1996).
Shepard et al., "Discoloration of Ceramic Hydroxyapatite Used for Protein Chromatography," Journalof Chromatography A 891 :93-98 (2000).
Sinacola et al., "Rapid Refolding and Polishing of Single-Chain Antibodies from *Escherichia coli* Inclusion Bodies," Protein Expression and Purification 26:301-308 (2002).
Stanker et al., "One-Step Purification of Mouse Monoclonal Antibodies from Ascites Fluid by Hydroxylapatite Chromatography," Journal of Immunological Methods 76:157-169 (1985).
Steindl et al., "A Simple Method to Quantify *Staphylococcal* Protein A in the Presence of Human or AnimalIgG in Various Samples," Journal of Immunological Methods 235:61-69 (2000).

(Continued)

*Primary Examiner* — Yunsoo Kim

(57) ABSTRACT

This invention relates to the application of hydroxyapatite chromatography to the purification of at least one antibody from a preparation containing high molecular weight aggregates. Further, this invention relates to an integration of ceramic hydroxyapatite chromatography into a combination chromatographic protocol for the removal of high molecular weight aggregates from an antibody preparation.

21 Claims, 4 Drawing Sheets

(56) References Cited

OTHER PUBLICATIONS

Stevens et al., "Techniques for Purifying Monoclonal Antibodies," American Biotechnology Laboratory, 3(5):22-30 (1985).
Tarditi et al., "Selective High-Performance Liquid Chromatographic Purification of Bispecific Monoclonal Antibodies," Journal of Chromatography 599:13-20 (1992).
Usami et al., "The Effect of pH, Hydrogen Peroxide and Temperature on the Stability of Human Monoclonal Antibody," Journal of Pharmaceutical and Biomedical Analysis 14:1133-1140 (1996).
Vola et al., "Comparison of Two Different HPLC Hydroxylapatite Matrices for Resolution of IgG Idiotypes," BioTechniques 14(4):650-655 (1993).
Yazaki et al., "Mamalian Expression and Hollow Fiber Bioreactor Production of Recombinant Anti-CEA Diabody and Minibody for Clinical Applications," Journal of Immunological Methods 253: 195-208 (2001 ).
Williams et al., Current Protocols in Protein Sciences, 1999, p. 8.2.1-8.2.30.
International Search Report and Written Opinion for PCT/US2004/032883, dated May 23, 2005.
Josic et al., •Purification of Monoclonal Antibodies by Hydroxylapatite HPLC and Size Exclusion HPLC; Biological Chemistry Hoppa-Seyler 372:149-156 (1991).
Giovannini et al., "Comparison of Different Types of Ceramic Hydroxyapatite for the Chromatographic Separation of Plasmid DNA and a Recombinant Anti-Rhesus D Antibody," Bioseparation 9:359-368 (2000).

* cited by examiner

REMOVAL OF HIGH MOLECULAR WEIGHT AGGREGATES USING HYDROXYAPATITE CHROMATOGRAPHY

This application is a continuation application of U.S. patent application Ser. No. 10/958,595, filed Oct. 6, 2004, which claims the benefit of U.S. Provisional Patent Application No. 60/523,335, filed Nov. 20, 2003, and U.S. Provisional Application No. 60/514,018, filed Oct. 27, 2003, the disclosures of which are hereby incorporated by reference in their entirety.

FIELD OF THE INVENTION

This invention relates to methods of removing high molecular weight aggregates from an antibody preparation using hydroxyapatite chromatography. In certain embodiments of this invention, the amount of high molecular weight aggregates present in the final preparation can be reduced significantly, such as from 40% to less than 1%.

BACKGROUND OF THE INVENTION

It is desirable to identify useful methods of purifying proteins that do not destroy, or significantly reduce, the biological activity of the protein. Contaminants must be removed from antibody preparations before they can be used in diagnostic applications, therapeutic applications, applied cell biology, and functional studies. Antibody preparations harvested from hybridoma cell lines, for instance, often contain unwanted components, such as high molecular weight aggregates (HMWA) of the antibody produced by the cell line. This formation of aggregates can adversely affect product safety by causing complement activation or anaphylaxis upon administration. Further, aggregate formation may hinder manufacturing processes by causing decreased product yield, peak broadening, and loss of activity.

The most common protein purification methods are predicated on differences in the size, charge, and solubility between the protein to be purified and contaminants. Protocols based on these parameters include affinity chromatography, ion exchange chromatography, size exclusion chromatography, and hydrophobic interaction chromatography. These chromatographic methods, however, sometimes present technical difficulties in the separation of aggregated or multimeric species of antibodies. Techniques such as ion exchange and hydrophobic interaction chromatography, for instance, may induce the formation of aggregates due to an increased protein concentration or the required changes in buffer concentration and/or pH during elution. Further, in several instances antibodies show differences in isoelectric points that are too small to allow for their separation by ion-exchange chromatography. Tarditi, J. Immunol. Methods 599:13-20 (1992). Size exclusion chromatography is cumbersome and results in the significant dilution of the product, which is a hindrance in large-scale, efficiency-based manufacturing processes. Leakage of ligands from affinity chromatography columns can also occur, which results in undesirable contamination of the eluted product. Steindl, J. Immunol. Methods 235:61-69 (2000). Applicants attempted to remove HMWA from an anti-GDF-8 antibody preparation using anion exchange chromatography, cation exchange chromatography, as well as hydrophobic interaction chromatography. However, all of these methods were unable to substantially remove the HMWA from the anti-GDF-8 antibody preparation.

Hydroxyapatite chromatography is a method of purifying proteins that utilizes an insoluble hydroxylated calcium phosphate $[Ca_{10}(PO_4)_6(OH)_2]$, which forms both the matrix and ligand. Functional groups consist of pairs of positively charged calcium ions (C-sites) and clusters of negatively charged phosphate groups (P-sites). The interactions between hydroxyapatite and proteins are complex and multimode. In one method of interaction, however, positively charged amino groups on proteins associate with the negatively charged P-sites and protein carboxyl groups interact by coordination complexation to C-sites. Shepard, J. of Chromatography 891:93-98 (2000).

Crystalline hydroxyapatite was the first type of hydroxyapatite used in chromatography, but it was limited by structural difficulties. Ceramic hydroxyapatite (cHA) chromatography was developed to overcome some of the difficulties associated with crystalline hydroxyapatite, such as limited flow rates. Ceramic hydroxyapatite has high durability, good protein binding capacity, and can be used at higher flow rates and pressures than crystalline hydroxyapatite. Vola et al., BioTechniques 14:650-655 (1993).

Hydroxyapatite has been used in the chromatographic separation of proteins, nucleic acids, as well as antibodies. In hydroxyapatite chromatography, the column is normally equilibrated, and the sample applied, in a low concentration of phosphate buffer and the adsorbed proteins are then eluted in a concentration gradient of phosphate buffer. Giovannini, Biotechnology and Bioengineering 73:522-529 (2000). Sometimes shallow gradients of sodium phosphate are successfully used to elute proteins, while in other instances concentration gradients up to 400 mM sodium phosphate have been used with success. See, e.g., Stanker, J. Immunological Methods 76:157-169 (1985) (10 mM to 30 mM sodium phosphate elution gradient); Shepard, J. Chromatography 891:93-98 (2000) (10 mM to 74 mM sodium phosphate elution gradient); Tarditi, J. Chromatography 599:13-20 (1992) (10 mM to 350 mM sodium phosphate elution gradient). While salts such as NaCl have been incorporated into the binding buffer to purify an antibody using hydroxyapatite chromatography, Giovannini, R. Biotechnology and Bioengineering 73:522-529 (2000), salts such as NaCl and $(NH_4)_2SO_4$ were not known to affect the elution of proteins in hydroxyapatite chromatography. Karlsson et al., Ion Exchange Chromatography, in Protein Purification, VCH Publishers, Inc. (Janson and Ryden eds., 1989).

In several instances, researchers have been unable to selectively elute antibodies from hydroxyapatite or found that hydroxyapatite chromatography did not result in a sufficiently pure product. Junbauer, J. Chromatography 476:257-268 (1989); Giovannini, Biotechnology and Bioengineering 73:522-529 (2000). Applicants unsuccessfully attempted to separate high molecular weight aggregates from an antibody preparation using ceramic hydroxyapatite chromatography and a sodium phosphate elution based on prior art teachings (FIG. 1). Further, harsh elution conditions, when used in an attempt to break the tight binding of a protein to a matrix, are known to destroy the biological activity of a protein. Thus, there is need for efficient methods of removing impurities, such as high molecular weight aggregates, from antibody preparations, which do not destroy the biological activity of the antibodies.

SUMMARY OF THE INVENTION

Applicants surprisingly found that NaCl can be utilized in a novel hydroxyapatite chromatography method for the purification of immunoglobulins and removal of HMWA from different raw materials (FIG. 2). Thus, the present invention relates to methods of removing high molecular weight aggregates from antibody preparations by contacting said preparation with a hydroxyapatite resin and selectively eluting the antibody from the resin. Alternatively, the antibody preparation may be buffer-exchanged into an equilibration buffer and then allowed to flow through a hydroxyapatite resin. A combination of these binding/flow-through hydroxyapatite chromatography methods may also be used to purify antibody preparations.

The invention features an elution buffer or load buffer that contains from 1 to 20 mM sodium phosphate and from 0.2 to 2.5 M NaCl, wherein the elution buffer or load buffer has a pH from 6.4 to 7.6.

In a combination binding/flow-through mode, the invention features an equilibration buffer and wash buffer that contain from 1 to 20 mM sodium phosphate, from 0.01 to 2.0 M NaCl, from 0 to 200 mM arginine, and from 0 to 200 mM HEPES, wherein the equilibration buffer and wash buffer have a pH from 6.2 to 8.0.

In one embodiment, the purified antibody contains less than 5% high molecular weight aggregates.

In a further embodiment, the purified antibody contains less than 1% high molecular weight aggregates.

In an additional embodiment, the antibody preparation contains at least one IgG antibody. More specifically, the antibody preparation contains at least one antibody chosen from anti-IL-21 receptor, anti-GDF-8, anti-Abeta, anti-CD22, anti-Lewis Y, anti-IL-13, or anti-IL-22.

At least one purification method may be used in combination with the hydroxyapatite chromatography of the invention. A variety of purification methods could be used, including, but not limited to, Protein A chromatography, affinity chromatography, hydrophobic interaction chromatography, immobilized metal affinity chromatography, size exclusion chromatography, diafiltration, ultrafiltration, viral removal filtration, anion exchange chromatography, and/or cation exchange chromatography.

In one embodiment, anion exchange and Protein A chromatography are used in combination with ceramic hydroxyapatite chromatography. Anion exchange and Protein A chromatography may be used in combination, for example, by contacting the antibody preparation with a Protein A support, allowing the antibody to adsorb to the support, washing the support and adsorbed antibody with at least one Protein A washing buffer, eluting the adsorbed antibody with at least one Protein A elution buffer, contacting the preparation with an ion exchange support, allowing the antibody to flow through the support, washing the support with at least one ion exchange washing buffer, contacting the ion exchange flow-through with a hydroxyapatite resin, allowing the flow-through to adsorb to the resin, washing the resin with at least one hydroxyapatite washing buffer, and eluting purified antibody from the resin with at least one hydroxyapatite elution buffer.

In a further embodiment, anion exchange and Protein A chromatography may be used in combination, for example, by contacting the preparation with a Protein A support, allowing the antibody to adsorb to the Protein A support, washing the Protein A support and adsorbed antibody with at least one Protein A washing buffer, eluting the adsorbed antibody with at least one Protein A elution buffer, contacting the Protein A eluate with an ion exchange support, allowing the antibody to flow through the ion exchange support, washing the ion exchange support with at least one ion exchange washing buffer, exchanging the ion exchange flow-through into a load buffer comprising from 1 to 20 mM sodium phosphate and from 0.2 to 2.5 M NaCl, contacting the ion exchange flow-through with a hydroxyapatite resin, allowing the antibody to flow through the hydroxyapatite resin, and washing the hydroxyapatite resin with at least one hydroxyapatite washing buffer.

In yet another embodiment, anion exchange and Protein A chromatography are used in combination with ceramic hydroxyapatite chromatography. Anion exchange and Protein A chromatography may be used in combination, for example, by contacting the antibody preparation with a Protein A support, allowing the antibody to adsorb to the support, washing the support and adsorbed antibody with at least one Protein A washing buffer, eluting the adsorbed antibody with at least one Protein A elution buffer, contacting the preparation with an ion exchange support, allowing the antibody to flow through the support, washing the support with at least one ion exchange washing buffer, contacting the ion exchange flow-through with a hydroxyapatite resin, allowing the flow-through to adsorb to the resin, allowing binding of the HMWA more tightly than antibody monomer and, as the loading continues, displacement of the bound monomer by the HMWA, washing the hydroxyapatite resin with at least one hydroxyapatite washing buffer, and collecting displaced antibody monomer.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute part of this specification, and together with the description, serve to explain the principles of the invention.

DETAILED DESCRIPTION OF THE INVENTION

A. Definitions

Figure 1:
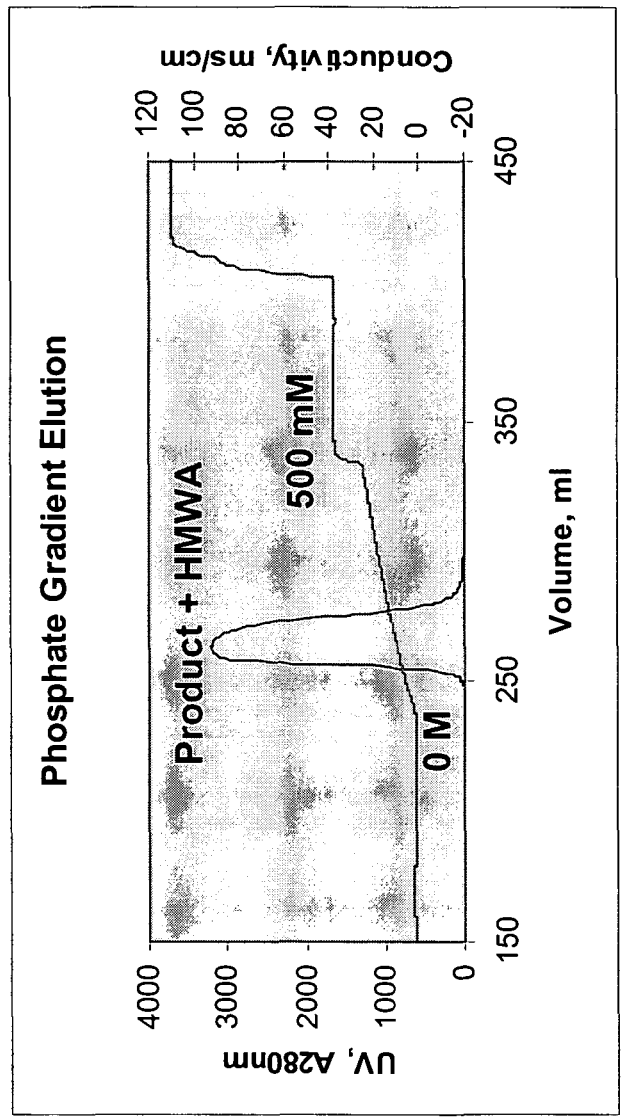
FIG. 1 demonstrates the inability of the prior art phosphate gradient elution to separate HMWA from an anti GDF-8 antibody preparation.
Figure 2:
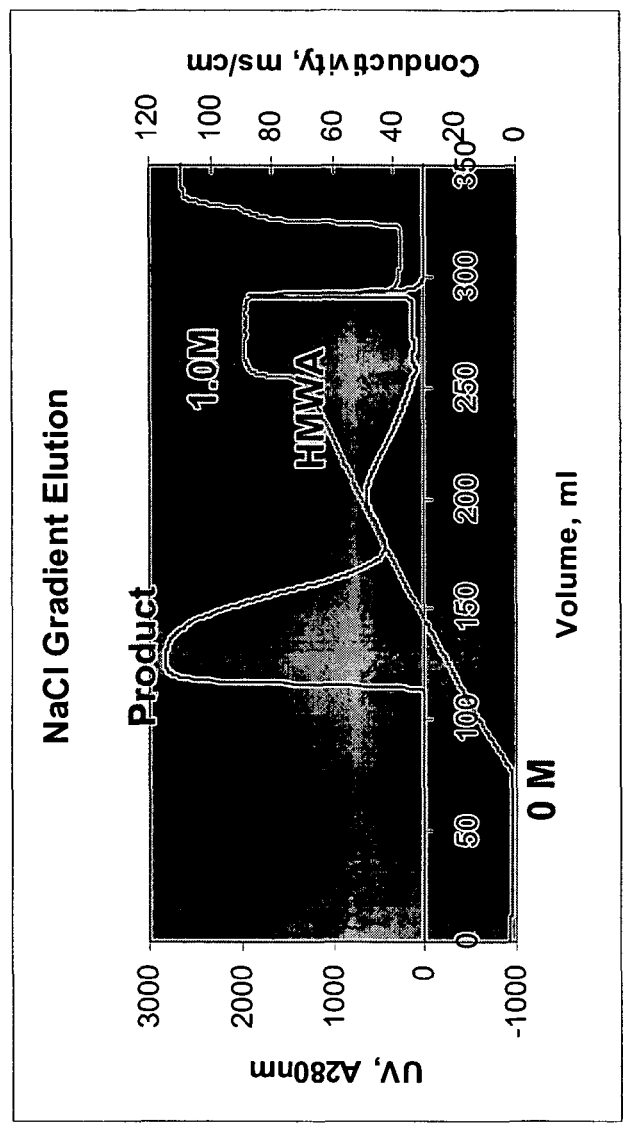
FIG. 2 demonstrates that use of NaCl gradient elution results in the separation of a large portion of the HMWA from an anti-GDF-8 antibody preparation.

In order that the present invention may be more readily understood, certain terms are first defined. Additional definitions are set forth throughout the detailed description.

The term "antibody" refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. The term "antibody" also includes antibody fragments such as Fab, F(ab')$_2$, Fv, scFv, Fd, dAb, and other antibody fragments that retain antigen-binding function. Typically, such fragments would comprise an antigen-binding domain.

Antibodies that may also be purified by the invention include chemically modified forms such as by PEG treatment, and fusion proteins comprising an immunoglobulin moiety. The antibody or fragment thereof may be selected from any of the known antibody isotypes and their conformations, for example, IgA, IgG, IgD, IgE, IgM monomers, IgA dimers, IgA trimers, or IgM pentamers.

The term "antibody preparation" refers to any composition containing an antibody and/or unwanted components, such as high molecular weight aggregates of such antibodies.

"Ceramic hydroxyapatite" or "cHA" refers to an insoluble hydroxylated calcium phosphate of the formula [$Ca_{10}(PO_4)_6(OH)_2$], which has been sintered at high temperatures into a spherical, macroporous ceramic form. The term "cHA" encompasses, but is not limited to, Type I and Type II ceramic hydroxyapatite. Unless specified, "cHA" refers to any particle size including, but not limited to, 20, 40, and 80 μm.

The term "high molecular weight aggregates" or "HMWA" refers to an association of at least two antibodies. The association may arise by any method including, but not limited to, covalent, non-covalent, disulfide, or nonreducible crosslinking. The at least two antibodies may bind to the same or different antigens. The at least two antibodies may be in the form of an antibody, antibody fragment, or other forms described in the definition of "antibody" above.

The term "flow-through mode" refers to an antibody preparation separation technique in which at least one antibody contained in the preparation is intended to flow through a chromatographic resin or support, while at least one potential contaminant or impurity binds to the chromatographic resin or support. Flow-through mode may be used, for instance, in hydroxyapatite chromatography and ion exchange chromatography.

"Binding mode" refers to an antibody preparation separation technique in which at least one antibody contained in the preparation binds to a chromatographic resin or support, while at least one contaminant or impurity flows through. Binding mode may be used, for instance, in hydroxyapatite chromatography and ion exchange chromatography.

B. Description of the Method

The present invention provides methods for removing high molecular weight aggregates (HMWA) from antibody preparations using hydroxyapatite chromatography in binding mode, flow-through mode, or a combination thereof. The present invention has application to the large scale purification of antibody preparations.

In binding mode, the method uses a hydroxyapatite support charged with phosphate at neutral pH and low ionic strength to bind both the antibody and HMWA. The column is then washed with a phosphate buffer to remove loosely bound impurities. Next, the antibody is selectively eluted using a high ionic strength phosphate buffer containing 0.2 to 2.5 M NaCl at slightly acidic to slightly basic pH. HMWA is optionally subsequently washed off the resin using an even higher ionic strength and higher phosphate concentration buffer at neutral pH. Lastly, the resin is optionally regenerated using a sodium hydroxide and potassium phosphate solution.

In flow-through mode, an antibody preparation is buffer-exchanged into a load buffer containing 0.2 to 2.5 M NaCl at slightly acidic to slightly basic pH. The antibody preparation is then allowed to flow through a hydroxyapatite column, while impurities such as HMWA bind to the column. The column is optionally subsequently washed to allow additional purified antibodies to flow through the column. Lastly, the column may optionally be stripped and then regenerated using a sodium hydroxide and potassium phosphate solution.

In combination binding/flow-through mode, the antibody preparation is allowed to flow through a hydroxyapatite column, with both antibody monomer and HMWA binding initially. However, as the loading continues, incoming HMWA is able to bind more tightly than antibody monomer and therefore displaces bound monomer. Consequently, the displaced monomer flows through the column. The column is optionally subsequently washed to allow additional displaced antibodies to flow through the column. Lastly, the column may be optionally stripped with a high salt, high phosphate solution and then regenerated using a sodium hydroxide and potassium phosphate solution.

In one embodiment of the invention, the purified antibody contains less than 5% HMWA, in one embodiment, less than 3% HMWA, and in another embodiment, less then 1% HMWA.

1. The Antibodies

The antibody preparations of the invention can be isolated from a number of sources including, but not limited to, serum of immunized animals, ascites fluid, hybridoma or myeloma supernatants, conditioned media derived from culturing a recombinant cell line that expresses the antibody molecule and from all cell extracts of antibody-producing cells. In one embodiment of the invention, antibodies from conditioned cell culture media of a variety of antibody producing recombinant cell lines are purified. Although one may expect some variation from cell line to cell line and among the various antibody products, based on the disclosure herein, it is well within the purview of one of ordinary skill in this art to adapt the invention herein to a particular combination of antibody protein and producing cell line.

For purposes of illustration only, this invention was applied to the purification of several antibodies of the IgG isotype and basic pI. More specifically, this invention was applied to monoclonal antibodies against GDF-8 described by U.S. Patent Provisional Patent Application No. 60/419,964 (hereinafter "Myo-29"), monoclonal antibodies specifically reactive with the CD22 antigen described by U.S. patent application Ser. No. 10/428,894 (hereinafter "anti-CD22"), and monoclonal antibodies against Abeta antigen described by International Application No. PCT/US01/46587 (hereinafter "anti-Abeta"). The construction of recombinant systems for the production of Myo-29 and the CD22 and Abeta antibodies are detailed in the above-mentioned applications.

2. The Hydroxyapatite Resin

Various hydroxyapatite chromatographic resins are available commercially, and any available form of the material can be used in the practice of this invention. In one embodiment of the invention, the hydroxyapatite is in a crystalline form. Hydroxyapatites for use in this invention may be those that are agglomerated to form particles and sintered at high temperatures into a stable porous ceramic mass.

The particle size of the hydroxyapatite may vary widely, but a typical particle size ranges from 1 μm to 1,000 μm in diameter, and may be from 10 μm to 100 μm. In one embodiment of the invention, the particle size is 20 μm. In another embodiment of the invention, the particle size is 40 μm. In yet another embodiment of the invention, the particle size is 80 μm.

A number of chromatographic supports may be employed in the preparation of cHA columns, the most extensively used are Type I and Type II hydroxyapatite. Type I has a high protein binding capacity and better capacity for acidic proteins. Type II, however, has a lower protein binding capacity, but has better resolution of nucleic acids and certain proteins. The Type II material also has a very low affinity for albumin and is especially suitable for the purification of many species and classes of immunoglobulins. The choice of a particular hydroxyapatite type can be determined by the skilled artisan.

This invention may be used with hydroxyapatite resin that is loose, packed in a column, or in a continuous annual chromatograph. In one embodiment of the invention, ceramic hydroxyapatite resin is packed in a column. The choice of column dimensions can be determined by the skilled artisan. In one embodiment of the invention, a column diameter of at least 0.5 cm with a bed height of about 20 cm may be used for small scale purification. In an additional embodiment of the invention, a column diameter of from about 35 cm to about 60 cm may be used. In yet another embodiment of the invention, a column diameter of from 60 cm to 85 cm may be used. In certain embodiments of the invention, a slurry of ceramic hydroxyapatite resin in 200 mM $Na_2HPO_4$ solution at pH 9.0 may be used to pack the column at a constant flow rate of about 4 cm/min or with gravity.

2. Buffer Compositions and Loading Conditions

Before contacting the hydroxyapatite resin with the antibody preparation, it may be necessary to adjust parameters such as pH, ionic strength, and temperature and in some instances the addition of substances of different kinds. Thus, it is an optional step to perform an equilibration of the hydroxyapatite matrix by washing it with a solution (e.g., a buffer for adjusting pH, ionic strength, etc., or for the introduction of a detergent) bringing the necessary characteristics for purification of the antibody preparation.

In combination binding/flow-through mode hydroxyapatite chromatography, the hydroxyapatite matrix is equilibrated and washed with a solution, thereby bringing the necessary characteristics for purification of the antibody preparation. In one embodiment of the invention, the matrix may be equilibrated using a solution containing from 0.01 to 2.0 M NaCl at slightly basic to slightly acidic pH. For example, the equilibration buffer may contain 1 to 20 mM sodium phosphate, in another embodiment it may contain 1 to 10 mM sodium phosphate, in another embodiment it may contain 2 to 5 mM sodium phosphate, in another embodiment it may contain 2 mM sodium phosphate, and in another embodiment may contain 5 mM sodium phosphate. The equilibration buffer may contain 0.01 to 2.0 M NaCl, in one embodiment, 0.025 to 0.5 M NaCl, in another embodiment, 0.05 M NaCl, and in another embodiment, 0.1 M NaCl. The pH of the load buffer may range from 6.2 to 8.0. In one embodiment, the pH may be from 6.6 to 7.7, and in another embodiment the pH may be 7.3. The equilibration buffer may contain 0 to 200 mM arginine, in another embodiment it may contain 120 mM arginine, and in another embodiment it may contain 100 mM arginine. The equilibration buffer may contain 0 to 200 mM HEPES, in another embodiment it may contain 20 mM HEPES, and in another embodiment it may contain 100 mM HEPES.

The antibody preparation may also be buffer exchanged into an appropriate buffer or load buffer in preparation for flow-through mode hydroxyapatite chromatography. In one embodiment of the invention, the antibody preparation may be buffer exchanged into a load buffer containing 0.2 to 2.5 M NaCl at slightly acidic to slightly basic pH. For example, the load buffer may contain 1 to 20 mM sodium phosphate, in another embodiment it may contain 2 to 8 mM sodium phosphate, in another embodiment it may contain 3 to 7 mM sodium phosphate, and in another embodiment may contain 5 mM sodium phosphate. The load buffer may contain 0.2 to 2.5 M NaCl in one embodiment, 0.2 to 1.5 M NaCl, in another embodiment, 0.3 to 1.0 M NaCl, and in another embodiment, 350 mM NaCl. The pH of the load buffer may range from 6.4 to 7.6. In one embodiment, the pH may be from 6.5 to 7.0, and in another embodiment the pH may be 6.8.

The contacting of an antibody preparation to the hydroxyapatite resin in either binding mode, flow-through mode, or combinations thereof may be performed in a packed bed column, a fluidized/expanded bed column containing the solid phase matrix, and/or in a simple batch operation where the solid phase matrix is mixed with the solution for a certain time.

After contacting the hydroxyapatite resin with the antibody preparation there is optionally performed a washing procedure. However, in some cases where very high purity of the immunoglobulin is not critical or additional flow-through antibody is not required, the washing procedure may be omitted, saving a process-step as well as washing solution. The washing buffers employed will depend on the nature of the hydroxyapatite resin, the mode of hydroxyapatite chromatography being employed, and therefore can be determined by one of ordinary skill in the art. In flow-through mode and combination binding/flow-through mode, the purified antibody flow-through obtained after an optional wash of the column may be pooled with other purified antibody fractions.

In binding mode, the antibody may be eluted from the column after an optional washing procedure. For elution of the antibody from the column, this invention uses a high ionic strength phosphate buffer containing about 0.2 to 2.5 M NaCl at slightly acidic to slightly basic pH. For example, the elution buffer may contain 1 to 20 mM sodium phosphate, in another embodiment it may contain 2 to 8 mM sodium phosphate, in another embodiment it may contain 2 to 6 mM sodium phosphate, in another embodiment may contain 3 mM sodium phosphate, and in another embodiment may contain 5 mM sodium phosphate. The elution buffer may contain 0.2 to 2.5 M NaCl, in one embodiment, 0.2 to 1.5 M NaCl, in another embodiment, 0.3 to 1.1 M NaCl, in another embodiment, 1.0 M NaCl, and in another embodiment, 0.35 M NaCl. The pH of the elution buffer may range from 6.4 to 7.6. In one embodiment, the pH may be from 6.5 to 7.3, in another embodiment the pH may be 7.2, and in another embodiment the pH may be 6.8. The elution buffer may be altered for elution of the antibody from the column in a continuous or stepwise gradient.

In both binding, flow-through mode, and combinations thereof, a solid phase matrix may optionally be cleaned, i.e. stripped and regenerated, after elution or flow through of the antibody. This procedure is typically performed regularly to minimize the building up of impurities on the surface of the solid phase and/or to sterilize the matrix to avoid contamination of the product with microorganisms.

Buffer components may be adjusted according to the knowledge of the person of ordinary skill in the art. Sample buffer composition ranges and examples for binding mode, flow-through mode, and combination binding/flow-through mode are provided in Table 1, Table 2, and Table 3, respectively. Not all of the buffers or steps are necessary, but are provided for illustration only. For example, it may not be necessary to have two distinct equilibration steps, and it may not be necessary to strip, regenerate, or store the hydroxyapatite resin. A high throughput screen, as described in Example 11, may be used to efficiently optimize buffer conditions for cHA column chromatography.

TABLE 1

Example buffer composition ranges for binding mode

| Buffer | Composition Range | Example Composition(s) |
|---|---|---|
| Equilibration 1 | 10 mM to 500 mM Sodium Phosphate 1.0M NaCl pH 6.4 to 7.4 | 0.3M Sodium Phosphate 1.0M NaCl pH 6.8 |
| Equilibration 2 | 1 to 20 mM Sodium Phosphate 0 to 200 mM NaCl pH 6.4 to 7.4 | 5.0 mM Sodium Phosphate 50 mM NaCl pH 7.2 |
| Wash | 1 to 20 mM Sodium Phosphate 0 to 200 mM NaCl pH 6.4 to 7.4 | 5.0 mM Sodium Phosphate 50 mM NaCl pH 7.2 |
| Elution | 1 to 20 mM Sodium Phosphate 0.2 to 2.5M NaCl pH 6.4 to 7.6 | 5.0 mM Sodium Phosphate 350 mM NaCl pH 6.8; or 3.0 mM Sodium Phosphate 1.0M NaCl pH 7.2 |
| Strip | 10 mM to 500 mM Sodium Phosphate 1.0M NaCl pH 6.4 to 7.4 | 0.3M Sodium Phosphate 1.0M NaCl pH 6.8 |
| Regeneration | 0.5 to 1.0M Potassium Phosphate 1.0M NaOH | 0.5M Potassium Phosphate 1.0M NaOH |
| Storage | 10 to 50 mM NaOH | 20 mM NaOH |

TABLE 2

Example buffer composition ranges for flow-through mode

| Buffer | Composition Range | Example Composition |
|---|---|---|
| Equilibration 1 | 10 mM to 500 mM Sodium Phosphate 1.0M NaCl pH 6.4 to 7.4 | 0.3M Sodium Phosphate 1.0M NaCl pH 6.8 |
| Equilibration 2 | 1 to 20 mM Sodium Phosphate 0.2 to 2.5M NaCl pH 6.4 to 7.6 | 5.0 mM Sodium Phosphate 350 mM NaCl pH 6.8 |
| Load buffer | 1 to 20 mM Sodium Phosphate 0.2 to 2.5M NaCl pH 6.4 to 7.6 | 5.0 mM Sodium Phosphate 350 mM NaCl pH 6.8 |
| Wash | 1 to 20 mM Sodium Phosphate 0.2 to 2.5M NaCl pH 6.4 to 7.6 | 5.0 mM Sodium Phosphate 350 mM NaCl pH 6.8 |
| Strip | 10 mM to 500 mM Sodium Phosphate 1.0M NaCl pH 6.4 to 7.4 | 0.3M Sodium Phosphate 1.0M NaCl pH 6.8 |
| Regeneration | 0.5 to 1.0M Potassium Phosphate 1.0M NaOH | 0.5M Potassium Phosphate 1.0M NaOH |
| Storage | 10 to 50 mM NaOH | 20 mM NaOH |

TABLE 3

Example buffer composition ranges for combination binding/flow-through mode

| Buffer | Composition Range | Example Composition(s) |
|---|---|---|
| Equilibration 1 | 10 mM to 500 mM Sodium Phosphate 1.0M NaCl pH 6.4 to 7.4 | 0.3M Sodium Phosphate 1.0M NaCl pH 6.8 |
| Equilibration 2 | 1 to 20 mM Sodium Phosphate 0.01 to 2.0M NaCl 0 to 200 mM Arginine 0 to 200 mM HEPES pH 6.2 to 8.0 | 2.0 mM Sodium Phosphate 50 mM NaCl, 100 mM Arginine 100 mM HEPES, pH 7.3; or 5.0 mM Sodium Phosphate 100 mM NaCl, 120 mM Arginine, 20 mM HEPES, pH 7.3 |
| Wash | 1 to 20 mM Sodium Phosphate 0.01 to 2.0M NaCl 0 to 200 mM Arginine 0 to 200 mM HEPES pH 6.2 to 8.0 | 2.0 mM Sodium Phosphate 50 mM NaCl, 100 mM Arginine 100 mM HEPES, pH 7.3; or 5.0 mM Sodium Phosphate 100 mM NaCl, 120 mM Arginine, 20 mM HEPES, pH 7.3 |
| Strip | 10 mM to 500 mM Sodium Phosphate 1.0M NaCl pH 6.4 to 7.4 | 0.3M Sodium Phosphate 1.0M NaCl pH 6.8 |
| Regeneration | 0.5 to 1.0M Potassium Phosphate 1.0M NaOH | 0.5M Potassium Phosphate 1.0M NaOH |
| Storage | 10 to 50 mM NaOH | 20 mM NaOH |

In one embodiment of the invention, the load onto the cHA resin may be, for instance, at a load challenge of ≤20 mg/ml and a starting aggregate level in the load of ≤40% HMWA. In certain embodiments of the invention, a load challenge of from 1.8 to 10.4 mg/ml may be used with a starting aggregate level in the load of about 15%.

In an additional embodiment of the invention, the cHA resin is loaded at a load challenge of at least 20 mg/ml and a starting aggregate level in the load of ≤40% HMWA. In certain embodiments of the invention, a load challenge of from 30 to 40 mg/ml may be used with a starting aggregate level in the load of about 27%.

3. Additional Optional Steps

Although it has been discovered that hydroxyapatite chromatography can be used alone to separate monomeric IgG from aggregates, as mentioned above, the purification method of the invention can be used in combination with other protein purification techniques. In one embodiment of the invention, one or more steps preceding the hydroxyapatite step may be desirable to reduce the load challenge of the contaminants or impurities. In another embodiment of the invention, one or more purification steps following the hydroxyapatite step may be desirable to remove additional contaminants or impurities.

The cHA purification procedure described may optionally be combined with other purification steps, including but not limited to, Protein A chromatography, affinity chromatography, hydrophobic interaction chromatography, immobilized metal affinity chromatography, size exclusion chromatography, diafiltration, ultrafiltration, viral removal filtration, and/or ion exchange chromatography.

In one embodiment, prior to the cHA purification step, the harvest media may optionally be initially purified by a Protein A chromatography step. For example, PROSEP-A™ (Millipore, U.K.), which consists of Protein A covalently coupled to controlled pore glass, can be usefully employed. Other useful Protein A formulations include Protein A Sepharose FAST FLOW™ (Amersham Biosciences, Piscataway, N.J.), TOYOPEARL™ 650M Protein A (TosoHaas Co., Philadelphia, Pa.), and MABSELECT™ columns (Amersham Biosciences, Piscataway, N.J.).

As an optional step prior to the cHA purification, ion exchange chromatography may be employed. In this regard various anionic or cationic substituents may be attached to matrices in order to form anionic or cationic supports for chromatography. Anionic exchange substituents include diethylaminoethyl (DEAE), trimethylaminoethyl acrylamide (TMAE), quaternary aminoethyl (QAE) and quaternary amine (Q) groups. Cationic exchange substituents include carboxymethyl (CM), sulfoethyl (SE), sulfopropyl (SP), phosphate (P) and sulfonate (S). Cellulosic ion exchange resins such as DE23, DE32, DE52, CM-23, CM-32 and CM-52 are available from Whatman Ltd. Maidstone, Kent, U.K. Sephadex-based and cross-linked ion exchangers are also known. For example, DEAE-, QAE-, CM-, and SP-Sephadex, and DEAE-, Q-, CM- and S-Sepharose, and Sepharose are all available from Amersham Biosciences, Piscataway, N.J. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa.

In one embodiment of the invention, ion exchange chromatography may be used in binding mode or flow-through mode.

In certain embodiments, the Protein A chromatography step is conducted first, the anion exchange step is conducted second, and the cHA step is conducted third.

4. Removal of Additional Impurities

In addition to HMWA removal, cHA chromatography has been shown useful in removing other impurities from antibody preparations. Other impurities that may be removed by the cHA chromatography methods of the invention include, but are not limited to, DNA, host cell protein, adventitious viruses, and Protein A contaminants from prior purification steps.

In one embodiment of the invention, the invention is able to remove Protein A from the antibody preparation. In certain embodiments of this invention, the amount of Protein A present in the final preparation can be reduced significantly, such as from 300 ppm to less than 1 ppm.

C. Examples

The following examples are offered for illustrative purposes only.

EXAMPLE 1

Purification of an Anti-GDF-8 Antibody

The purification process outlined below was developed for an anti-GDF-8 monoclonal antibody (referred to herein as "Myo-29"). The Myo-29 antibody is an IgG1 subtype antibody and has a pI of approximately 8.1. The purification process was comprised of three chromatographic steps (Protein A affinity, anion exchange, and hydroxyapatite), a viral inactivation step, and an ultrafiltration/diafiltration step to concentrate and exchange the product into a final buffer. All steps were performed at 18 to 25° C., except the Protein A chromatography step, which was run at 2 to 8° C.

The purification process can be normalized for any scale. Linear flow rates listed are independent of column diameter and loading ratios are in mass per unit volume. The Protein A chromatography step can be cycled multiple times per batch to accommodate varying amounts of cell culture titer in the harvest bioreactor. Each cycle is considered a separate unit operation and the elution pool is held for the next step. The Protein A step has a capacity of approximately 35 grams Myo-29 per liter of MabSelect. The downstream steps of the process (e.g., anion exchange chromatography and ceramic hydroxyapatite chromatography) are scaled to accommodate approximately 15 grams Myo-29 per liter of anion exchange resin and around 10 grams of Myo-29 per liter of ceramic hydroxyapatite resin.

1. Removal of Cells from the Culture

The Myo-29 antibody was expressed in Chinese Hamster Ovary (CHO) cells and was grown in a stirred 2500 L tank bioreactor. To harvest the culture fluid, the cells were removed using a Prostak microfiltration device (Millipore, Billerica, Mass.). The clarified conditioned media (CCM) was collected for the first chromatographic step, Protein A chromatography.

2. Protein A Affinity Chromatography Purification Step

A 17.7 L (30 cm diameter×25 cm height) MabSelect column of recombinant Protein A resin (Amersham Biosciences, Piscataway, N.J.) was equilibrated with 5 column volumes of an equilibration buffer (10 mM Tris, 100 mM NaCl, pH 7.5). The CCM was applied to the column at a 2.5 cm/min flow rate and a load challenge of 35 g Myo-29 per liter of resin. After loading the column, it was washed with 5 column volumes of a high salt wash buffer (20 mM Tris, 1.0 M NaCl, pH 7.5) and then with 10 column volumes of a low salt wash buffer (10 mM Tris, 100 mM NaCl, pH 7.5). The Myo-29 was eluted by applying 6 column volumes of an elution buffer (100 mM Arginine, 50 mM NaCl, pH 3.0). The elution pool was then held at a pH of 3.6±0.5 for 1.5±0.5 hours as a prophylactic measure to facilitate the inactivation of potential adventitious virus contaminants. The elution pool was then neutralized to pH 7.3 with 2 M HEPES buffer at pH 8.0, to prevent degradation of acid labile moieties of Myo-29.

Column effluents were monitored by several parameters, including visual inspection of UV absorbance and conductivity chromatographic profiles, and product recovery using Protein A HPLC for the load titer and absorbance at 280 nm for the elution pool concentration.

The column was stripped with 6 M Guanidine HCl and then washed with strip wash buffer (10 mM Tris, 100 mM NaCl, pH 7.5). The column was stored in 16% ethanol.

3. Anion Exchange Chromatography Purification Step

The Protein A column eluate was further purified by anion exchange chromatography on a 75 L column (80 cm diameter×15 cm length) of Q SEPHAROSE FF resin (Amersham Biosciences, Piscataway, N.J.). The column was equilibrated with 5 column volumes of a first equilibration buffer (20 mM HEPES, 1000 mM NaCl, pH 7.3) and then with 5 column volumes of a second equilibration buffer (100 mM Arginine, 50 mM NaCl, 100 mM HEPES, pH 7.3). The Protein A column eluate was applied to the equilibrated column at a flow rate of 2.5 cm/min and a load ratio of 15 grams Myo-29 per liter of resin. After loading, the column was washed with 5 column volumes of the second equilibration buffer. The anion exchange column flow-through was collected.

The collected column flow-through was monitored by several parameters, including visual inspection of UV absorbance and conductivity chromatographic profiles, and product recovery using absorbance at 280 nm.

The anion exchange column was stripped with strip buffer (20 mM HEPES, 1 M NaCl, pH 7.3) and regenerated with regeneration buffer (500 mM NaOH, 1 M NaCl, pH 13.3). The column was stored in 0.01 M NaOH.

4. Virus Retaining Filtration

The objective of this optional step was the removal of retroviral-like particles that may be present in CHO cell culture and to provide additional safety through the removal of potential adventitious virus contaminants. The anion exchange column flow-through was collected and passed through a 35 nm Planova single-use filter (Asahi-Kasei Corp., New York, N.Y.). Remaining product in the module was recovered by passing anion exchange column wash buffer (100 mM Arginine, 50 mM NaCl, 100 mM HEPES, pH 7.3) through the device.

The product recovery after virus retaining filtration was assessed by absorbance at 280 nm and SDS-PAGE analysis of the Planova pool in comparison with historical performance data.

5. cHA Chromatography Purification Step

The viral filtered solution was further purified with a hydroxyapatite column (60 cm×20 cm) packed with cHA Type II resin, 40 μM particle size (BioRad, Hercules, Calif.). The column was equilibrated with 3 column volumes of equilibration buffer 1 (0.3 M sodium phosphate, 1.0 M NaCl, pH 6.8). A second equilibration step was conducted with 4 column volumes of equilibration buffer 2 (5 mM sodium phosphate, 50 mM NaCl, pH 7.2). The partially purified media was loaded onto the resin in a loading buffer 1:1 (v/v) (10 mM sodium phosphate, pH 7.2) and at a flow rate of 2.5 cm/min. The cHA column was washed with 3 column volumes of a wash buffer (5 mM sodium phosphate, 50 mM NaCl, pH 7.2). The Myo-29 antibody was eluted from the cHA resin using 6 column volumes of an elution buffer (5 mM sodium phosphate, 350 mM NaCl, pH 6.8).

The cHA purification step was monitored by visual inspection of UV absorbance and conductivity chromatographic profiles, product recovery by absorbance at 280 nm, HMWA removal as determined by size exclusion chromatography (SEC) analysis, and Protein A removal as determined by a competitive enzyme linked immunosorbent assay (ELISA).

The cHA column was stripped with strip buffer (0.3 M sodium phosphate, 1.0 M NaCl, pH 6.8) and regenerated with regeneration buffer (0.5 M potassium phosphate, 1.0 M NaOH, pH 13.3). The column was stored in 0.02 M NaOH. Table 4 demonstrates that cHA chromatography effectively removes HMWA impurities from antibody preparations. Further, cHA chromatography is able to remove other impurities, such as Protein A.

TABLE 4

HMWA clearance and antibody monomer yields

| Sample | % HMWA Load | % HMWA Peak | ProA Load (ppm) | ProA Peak |
|---|---|---|---|---|
| 1 | 14.6 | 1.0 | 17 | BLOQ* |
| 2 | 16.4 | 0.7 | 20 | BLOQ |
| 3 | 15.1 | 1.6 | 23 | BLOQ |
| 4 | 16.0 | 0.9 | 13 | BLOQ |

*BLOQ = Below limit of quantitation of 1 ng/ml.

6. Ultrafiltration/Diafiltration and Final Filtration

The cHA elution pool was passed through a tangential flow ultrafiltration system using PLCTK Pellicon 2 cassettes (Millipore, Billerica, Mass.) composed of a composite regenerated cellulose membrane with a 30,000 nominal molecular weight limit. The objectives of this step were to concentrate and buffer exchange the cHA product pool into the formulation buffer. The cHA product pool was spiked with a 50% sucrose solution (w/v) to bring the concentration of sucrose to 2%. Myo-29 antibody was concentrated to approximately 20 gL$^{-1}$, then diafiltered with approximately ≥9 wash volumes of formulation buffer (0.01 M L-Histidine, 2% Sucrose, pH 6.0). Upon completion of the diafiltration, the product was further concentrated to approximately 60 gL$^{-1}$ and recovered from the apparatus by gravity drain and an air blow down followed by flushing the retentate channels with formulation buffer. The concentration target of the Myo-29 in Drug Substance is ≥35 g/L.

The Myo-29 drug substance was finally filtered through a 0.22 micron filter, equilibrated with formulation buffer (0.01 M L-Histidine, 2% Sucrose, pH 6.0), aliquoted into bottles, and then stored at −80° C.

EXAMPLE 2 cHA Purification of an Anti-GDF-8 Antibody Preparation using Type I Resin

The Myo-29 antibody was also successfully purified using Type I cHA resin, 40 μM particle size, packed in a 3.1 L column. The column was equilibrated with 3 column volumes of equilibration buffer 1 (0.3 M sodium phosphate, 1.0 M NaCl, pH 6.8). A second equilibration step was conducted with 4 column volumes of equilibration buffer 2 (5 mM sodium phosphate, 50 mM NaCl, pH 7.2). Partially purified media from an anion exchange purification step was loaded onto the resin at a load challenge of 35 mg/ml and at a flow rate of 1.5 cm/min. The cHA column was washed with 3 column volumes of a wash buffer (5 mM sodium phosphate, 50 mM NaCl, pH 7.2). The Myo-29 antibody was eluted from the cHA resin using 6 column volumes of an elution buffer (3 mM sodium phosphate, 1.0 M NaCl, pH 7.2).

The cHA column was stripped with strip buffer (0.3 M sodium phosphate, 1.0 M NaCl, pH 6.8) and regenerated with regeneration buffer (0.5 M potassium phosphate, 1.0 M NaOH, pH 13.3). The column was stored in 0.02 M NaOH.

The cHA purification step was monitored by visual inspection of UV absorbance and conductivity chromatographic profiles, product recovery by absorbance at 280 nm, HMWA removal as determined by size exclusion chromatography (SEC) analysis, and Protein A removal as determined by a competitive enzyme linked immunosorbent assay (ELISA). As shown in Table 5, cHA purification using Type I resin was able to decrease the percentage of HMWA from 27% to 0.9% in the first cycle, and further decrease the HMWA percentage to 0.6% in the second cycle. In addition, Type I resin accommodated a higher load challenge than that of Type II resin, while still producing sufficient monomer yield. Finally, cHA purification using Type I resin is able to decrease the amount of Protein A impurity.

TABLE 5

HMWA clearance and antibody monomer yields using Type I resin

| Sample | % HMWA | % Monomer Yield | Protein A (ppm) |
|---|---|---|---|
| cHA Load | 27.0 | N/A | 169 |
| cHA Peak (cycle #1) | 0.9 | 86.6 | BLOQ* |
| cHA Peak (cycle #2) | 0.6 | 86.6 | BLOQ |

*BLOQ = Below limit of quantitation of 1 ng/ml

EXAMPLE 3 cHA Purification of an Anti-CD22 Antibody Preparation and an Anti-Abeta Antibody Preparation using Type I Resin The cHA purification process described in Example 2 was also able to sufficiently remove HMWA from both an anti-CD22 and an anti-Abeta antibody preparation. The process used was similar to that described in Example 2, with the exception that the purified antibody monomer was gradient-eluted in 15 column volumes of elution buffer (3 mM sodium phosphate, 1.5 M NaCl, pH 7.2).

As demonstrated in Table 6, cHA purification using Type I resin was able to decrease HMWA in the anti-CD22 antibody preparation to 0.5% and in the anti-Abeta antibody preparation to below the limit of detection. Further, the cHA purification step was able to remove Protein A contaminants from the antibody preparation.

TABLE 6

HMWA clearance and antibody monomer yields using Type I resin in purification of anti-CD22 and anti-Abeta antibody preparations

| Sample | % HMWA | % Monomer Yield | Protein A (ppm) |
|---|---|---|---|
| Anti-CD22 Load | 3.7 | N/A | 30 |
| Anti-CD22 Peak | 0.5 | 87 | BLOQ* |
| Anti-Abeta Load | 1.87 | N/A | 40 |
| Anti-Abeta Peak | 0.0 | 89 | BLOQ |

*BLOQ = Below limit of quantitation of 1 ng/ml

EXAMPLE 4

Flow-Through Mode cHA Purification of an Anti-GDF-8 Antibody

The Myo-29 antibody was also successfully purified using a flow-through mode cHA purification protocol. A 1.6×20 cm Vantage column (Millipore, Billerica, Mass.) was packed in 200 mM sodium phosphate dibasic, pH 9.0 using Macro-Prep Ceramic Hydroxyapatite Type II, 40 μM particle size resin (BioRad, Hercules, Calif.). The column was equilibrated with 3 column volumes of equilibration buffer 1 (300 mM sodium phosphate, 1.0 M NaCl, pH 6.8) and 3 column volumes of equilibration buffer 2 (350 mM NaCl, 5 mM sodium phosphate, pH 6.8). Myo-29 antibody preparation was buffer-exchanged into a load buffer containing 350 mM NaCl, 5 mM sodium phosphate, pH 6.8 and then loaded onto the cHA column. The column was washed with wash buffer (350 mM NaCl, 5 mM sodium phosphate, pH 6.8), stripped with strip buffer (300 mM sodium phosphate, 1.0 M NaCl, pH 6.8), and then regenerated with regeneration buffer (500 mM potassium phosphate, 1.0 M NaOH, pH 13.3). All flow rates were kept at 2.5 to 3 cm/min. Column effluents were analyzed by SEC-HPLC using a HPLC system.

A summary of the Myo-29 recovery and removal of HMWA from the antibody preparation is presented in Table 7. The preparation initially contained 14.4% HMWA (load), which was reduced to 0.2% HMWA (flow-through) using the cHA purification method of the invention.

TABLE 7

Myo-29 recovery and HMWA removal

| Sample | % Myo-29 Recovery | % HMWA in Sample |
|---|---|---|
| Load | N/A | 14.4 |
| Flow-through | 79.6 | 0.2 |
| Wash | 12.2 | 1.9 |
| Post-wash | 1.5 | 5.6 |
| Strip | 10.3 | 84.3 |

EXAMPLE 5

Flow-Through Mode cHA Purification of an Anti-GDF-8 Antibody Using Type I Resin A 1.1×21 cm Vantage column (Millipore, Billerica, Mass.) was packed in 200 mM sodium phosphate dibasic, pH 9.0 using Macro-Prep Ceramic Hydroxyapatite Type I, 40 μM particle size resin (BioRad, Hercules, Calif.). The column was equilibrated with 3 column volumes of equilibration buffer 1 (300 mM sodium phosphate, 1.0 M NaCl, pH 6.8) and 3 column volumes of equilibration buffer 2 (1.0 M NaCl, 3 mM sodium phosphate, pH 7.2). Myo-29 antibody preparation was buffer-exchanged into a load buffer containing 1.0 M NaCl, 3 mM sodium phosphate, pH 7.2 and then loaded onto the cHA column at a load challenge of 26 mg/ml. The column was washed with wash buffer (1.0 M NaCl, 3 mM sodium phosphate, pH 7.2), stripped with strip buffer (300 mM sodium phosphate, 1.0 M NaCl, pH 6.8), and then regenerated with 5 column volumes of regeneration buffer (500 mM potassium phosphate, 1.0 M NaOH, pH 13.3). Flow rates were kept at less than 90 cm/hr for the load and wash and less than 240 cm/hr for the rest of the purification process. Column effluents were analyzed by SEC-HPLC using a HPLC system.

The antibody preparation initially contained 27.2% HMWA (load), which was reduced to 6.1% HMWA (flow-through). Further, the recovery of antibody monomer was 72%.

EXAMPLE 6 cHA Purification of an Anti-CD22 Antibody Preparation

Ceramic HA chromatography purification was also shown to be useful in purifying an anti-CD22 antibody preparation. A 1.6×20 cm Vantage column (Millipore, Billerica, Mass.) was packed in 200 mM sodium phosphate dibasic at pH 9.0 using Macro-Prep Ceramic Hydroxyapatite Type II, 40 μM particle size resin (BioRad, Hercules, Calif.). The column was equilibrated with 3 column volumes of equilibration buffer 1 (300 mM sodium phosphate, 1.0 M NaCl, pH 6.8) and 3 column volumes of equilibration buffer 2 (50 mM NaCl, 5 mM sodium phosphate, pH 6.8). An anti-CD22 antibody preparation was buffer-exchanged into 50 mM NaCl, 5 mM sodium phosphate, pH 6.8 and then loaded onto the cHA column. The column was washed with 3 column volumes of wash buffer (50 mM NaCl, 5 mM sodium phosphate, pH 6.8) and then gradient-eluted with 5 mM sodium phosphate, 1.0 M NaCl, pH 6.8 in 15 column volumes. The column was stripped with strip buffer (300 mM sodium phosphate, 1.0 M NaCl, pH 6.8) and then regenerated with regeneration buffer (500 mM potassium phosphate, 1.0 M NaOH). All flow rates were kept at 2.5 to 3 cm/min. Column effluents were analyzed by SEC-HPLC using a HPLC system.

Figure 3:
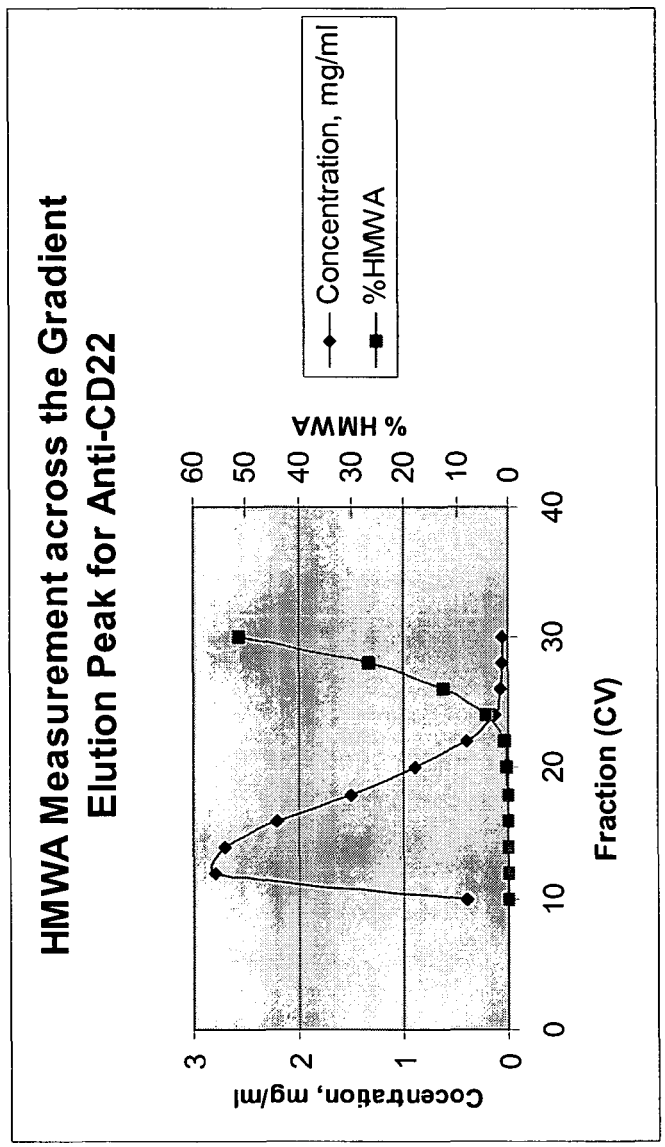
FIG. 3 shows the separation of HMWA from an anti-CD22 antibody preparation using cHA chromatography.

As shown in FIG. 3, the cHA purification was successful in removing HMWA from the anti-CD22 antibody preparation. The percentage HMWA in the load was 1.7%, while the percentage of HMWA in the cHA eluate was 0.0%.

EXAMPLE 7 cHA Purification of an Anti-Abeta Antibody

Ceramic HA chromatography purification was also shown to be useful in purifying an anti-Abeta antibody preparation. A 1.6×20 cm Vantage column (Millipore) was packed in 200 mM sodium phosphate dibasic at pH 9.0 using Macro-Prep Ceramic Hydroxyapatite Type II, 40 µM particle size resin (BioRad, Hercules, Calif.). The column was equilibrated with 3 column volumes of equilibration buffer 1 (300 mM sodium phosphate, 1.0 M NaCl, pH 6.8) and 5 column volumes of equilibration buffer 2 (50 mM NaCl, 5 mM sodium phosphate, pH 6.8). An anti-Abeta antibody preparation was buffer-exchanged into 50 mM NaCl, 5 mM sodium phosphate, pH 6.8 and then loaded onto the column. The column was washed with 5 column volumes of wash buffer (50 mM NaCl, 5 mM sodium phosphate, pH 6.8) and then gradient-eluted with 5 mM sodium phosphate, 1.0 M NaCl, pH 6.8 in 15 column volumes. The column was stripped with strip buffer (300 mM sodium phosphate, 1.0 M NaCl, pH 6.8) and then regenerated with regeneration buffer (500 mM potassium phosphate, 1.0 M NaOH). All flow rates are kept at 2.5 to 3 cm/min. Column effluents were analyzed by SEC-HPLC using a HPLC system.

Figure 4:
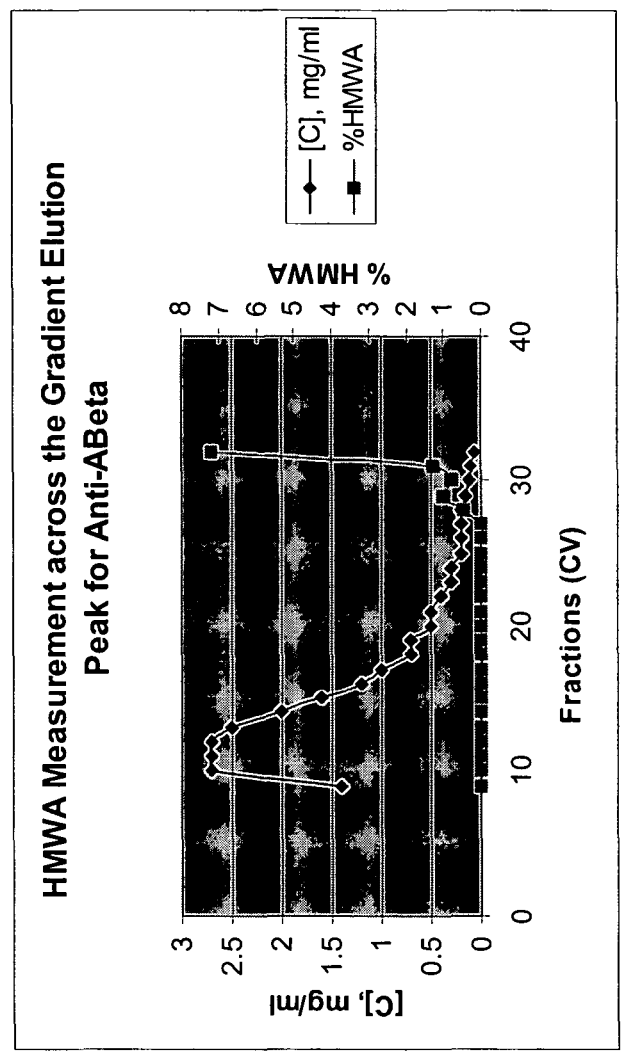
FIG. 4 shows the separation of HMWA from an anti-Abeta antibody preparation using cHA chromatography.

As shown in FIG. 4, the cHA purification was successful in removing HMWA from the anti-Abeta antibody preparation. The percentage HMWA in the load was 2.6%, while the percentage of HMWA in the cHA eluate was 0.0%.

EXAMPLE 8

Evaluation of the Activity of Purified Myo-29 Antibody

The anti-GDF-8 antibody purified according to the method described in Example 1, Myo-29, was assayed for binding activity using a competitive enzyme linked immunosorbent assay (ELISA). Competitive ELISA can be adapted to test the binding activity of other purified antibodies. See e.g., Antibodies: A Laboratory Manual, Harlow and Land (eds.), 1988, Cold Spring Harbor Laboratory Press, Cold Spring Harbor, N.Y. A GDF-8 receptor, ActRIIrβ.Fc (2 µg/mL), was adsorbed onto a 96-well microtiter plate in a volume of 100 µl/well. The plate was then incubated at 2 to 8° C. overnight. The plate was washed twice with wash buffer (50 mM Tris-HCl, pH 8.0, 0.05% Tween 20) and blocked with a 4% solution of bovine serum albumin (BSA) to minimize non-specific binding. The plate was incubated at room temperature for 1.5 to 3.0 hours and washed twice with wash buffer (50 mM Tris-HCl, pH 8.0, 0.05% Tween 20).

Myo-29 antibody reference standard was serially diluted 4-fold into assay diluent (0.5% BSA, 137 mM NaCl, 2.7 mM KCl), resulting in a total of 8 standards points. The test samples contained Myo-29 antibody fractions purified by a Protein A chromatography step as well as fractions purified after an additional cHA purification step. These test samples were also serially diluted 2-fold in assay diluent to result in 8 points that fell within the range of the standard curve. The standards and test samples were added to the appropriate assay wells at 50 µl/well. The biotinylated competitor, biotin labeled GDF-8 (50 ng/mL) was then added to each well at 50 µl/well. The plate was incubated overnight on a plate shaker at room temperature.

The plate was washed four times with wash buffer (50 mM Tris-HCl, pH 8.0, 0.05% Tween 20) and bound biotin labeled GDF-8 was detected with the addition of 100 µl/well streptavidin conjugated horseradish peroxidase (1:5,000; Southern Biotech, Birmingham, Ala.). The plate was incubated 50 to 70 minutes on the plate shaker at room temperature and then developed by adding 100 µl/well 3,3',5,5'-tetramethylbenzidine (BioFX, Owings Mills, Md.). The absorbance for each well is determined at 450 nm with an ELISA plate reader (Molecular Devices, Sunnyvale, Calif.). The amount of active Myo-29 in the test sample is indirectly proportional to the signal generated in the assay. The reaction was stopped by adding 100 µl/well 0.18 M $H_2SO_4$.

A concentration of Myo-29 capable of binding biotinylated GDF-8 in test samples was interpolated from the standard curve that had been fit using a 4-parameter logistic equation. Bioactivity value (% active protein) of a test sample was then computed by dividing the active protein concentration (determined by ELISA) by the total protein concentration (determined by $A_{280}$) and multiplying this ratio by 100. If the same sample was purified in separate batches, averages of the bioactivity value were calculated. The bioactivity values are reported in Table 8.

TABLE 8

Anti-GDF-8 antibody binding activity (% active protein)

| Sample | Post-Protein A Purification | Post-cHA Purification |
|---|---|---|
| 1 | 88 | 108 |
| 2 | 86 | 104 |
| 3 | 94 | 108 |

As demonstrated in Table 8, the Myo-29 retains its ability to bind GDF-8 after being purified by the process described in Example 1. The binding activity of purified Myo-29 is somewhat lower in the peak eluant fractions from the Protein A purification. However, the binding activity exceeds the reference Myo-29 antibody after an additional cHA purification step as described in Example 1.

EXAMPLE 9

Combination Binding/Flow-Through Mode cHA Purification of an Anti-GDF-8 Antibody Ceramic HA chromatography purification in a combination binding/flow-through mode was also shown to be useful in purifying an anti-GDF-8 antibody preparation. The experiment detailed below was run on an ÄKTA FPLC system (General Electric). A 1.1×21 cm Vantage column (Millipore) was packed in 200 mM sodium phosphate dibasic at pH 9.0 using Macro-Prep Ceramic Hydroxyapatite Type II, 40 µM particle size resin (BioRad, Hercules, Calif.). The column was equilibrated with 3 column volumes of equilibration buffer 1 (300 mM sodium phosphate, 1.0 M NaCl, pH 6.8) and 5 column volumes of equilibration buffer 2 (50 mM NaCl, 2.0 mM sodium phosphate, 100 mM arginine, 100 mM HEPES, pH 7.3). An anti-GDF-8 antibody preparation was loaded onto the column with a load challenge of 20 mg/ml. The column was washed with equilibration buffer 2, stripped with strip buffer (300 mM sodium phosphate, 1.0 M NaCl, pH 6.8), and then regenerated with regeneration buffer (500 mM potassium phosphate, 1.0 M NaOH, pH 13.3). The flow rate for load and wash was 1.5 cm/min. Flow rates for the rest of the purification process were kept at 2.5 to 3.0 cm/min. Column effluents were analyzed by SEC-HPLC using a HPLC system.

Results demonstrated that operation of the cHA Type II resin in the combination binding/flow-through mode is effective in removing HMWA from antibody preparations. The preparation initially contained 27% HMWA (load), which was reduced to 1.1% HMWA (flow-through) using the cHA purification method of the invention.

EXAMPLE 10

Combination Binding/Flow-Through Mode cHA Purification of an Anti-GDF-8 Antibody using Type I Resin The procedure described in Example 9 was repeated using Type I cHA resin in place of Type II cHA resin. The buffer conditions were identical to those used in Example 9, with the exception of the equilibration buffer 2, which was composed of 5.0 mM sodium phosphate, 100 mM NaCl, 120 mM Arginine, 20 mM HEPES, at a pH of 7.3.

As shown in Table 9, operation of the cHA Type I resin in combination binding/flow-through mode is effective in removing HMWA from antibody preparations while maintaining antibody monomer yields. Further, combination binding/flow-through mode is effective in removing Protein A impurities. Finally, Type I cHA resin allowed for an increased load challenge of 55 mg/ml.

TABLE 9

HMWA clearance and antibody monomer yields from the cHA Type I resin operated in the combination binding/flow-through mode

| Sample | | % HMWA | % Monomer Yield | Protein A (ppm) |
|---|---|---|---|---|
| Run 1 | Load | 27.0 | NA | 236 |
| | Peak | 0.9 | 75 | 3.3 |
| Run 2 | Load | 27.2 | NA | — |
| | Peak | 0.7 | 78 | — |

EXAMPLE 11

High Throughput Screen of cHA Buffer Conditions

A high throughput screen was performed to optimize the buffer conditions used to purify a Myo-029 antibody preparation using cHA-Type I resin. The screen varied the levels of sodium phosphate, sodium chloride, arginine and Myo-029 on the cHA-Type I resin and examined the extent of binding of Myo-029 and the high molecular weight aggregate (HMWA) to the resin.

cHA Type I resin (50 µL) was added to each well of a 96 well filter plate. Each well, labeled A1, A2 . . . H11, H12 in Tables 10-12, was equilibrated in equilibration buffer made up of 20 mM HEPES, pH 7.2 and a unique combination of phosphate (Table 10), sodium chloride (Table 11), and arginine (Table 12).

TABLE 10

Phosphate levels in each well

| | 1 | 2 | 3 | 4 | 5 | 6 | 7 | 8 | 9 | 10 | 11 | 12 |
|---|---|---|---|---|---|---|---|---|---|---|---|---|
| A | 1 mM | 1 mM | 1 mM | 6 mM | 5 mM | 4 mM | 1 mM | 1 mM | 1 mM | 3 mM | 2 mM | 1 mM |
| B | 1 mM | 1 mM | 1 mM | 6 mM | 5 mM | 4 mM | 1 mM | 1 mM | 1 mM | 3 mM | 2 mM | 1 mM |
| C | 1 mM | 1 mM | 1 mM | 6 mM | 5 mM | 4 mM | 1 mM | 1 mM | 1 mM | 3 mM | 2 mM | 1 mM |
| D | 1 mM | 1 mM | 1 mM | 6 mM | 5 mM | 4 mM | 1 mM | 1 mM | 1 mM | 3 mM | 2 mM | 1 mM |
| E | 2 mM | 3 mM | 4 mM | 8 mM | 10 mM | 16 mM | 2 mM | 3 mM | 4 mM | 5 mM | 6 mM | 8 mM |
| F | 2 mM | 3 mM | 4 mM | 8 mM | 10 mM | 16 mM | 2 mM | 3 mM | 4 mM | 5 mM | 6 mM | 8 mM |
| G | 2 mM | 3 mM | 4 mM | 8 mM | 10 mM | 16 mM | 2 mM | 3 mM | 4 mM | 5 mM | 6 mM | 8 mM |
| H | 2 mM | 3 mM | 4 mM | 8 mM | 10 mM | 16 mM | 2 mM | 3 mM | 4 mM | 5 mM | 6 mM | 8 mM |

TABLE 11

NaCl levels in each well

| | 1 | 2 | 3 | 4 | 5 | 6 | 7 | 8 | 9 | 10 | 11 | 12 |
|---|---|---|---|---|---|---|---|---|---|---|---|---|
| A | 25 mM | 25 mM | 25 mM | 25 mM | 25 mM | 25 mM | 750 mM | 625 mM | 500 mM | 500 mM | 400 mM | 300 mM |
| B | 25 mM | 25 mM | 25 mM | 25 mM | 25 mM | 25 mM | 750 mM | 625 mM | 500 mM | 500 mM | 400 mM | 300 mM |
| C | 50 mM | 100 mM | 200 mM | 50 mM | 100 mM | 200 mM | 1,250 mM | 1,750 mM | 2,500 mM | 600 mM | 800 mM | 1,000 mM |
| D | 50 mM | 100 mM | 200 mM | 50 mM | 100 mM | 200 mM | 1,250 mM | 1,750 mM | 2,500 mM | 600 mM | 800 mM | 1,000 mM |
| E | 25 mM | 25 mM | 25 mM | 25 mM | 25 mM | 25 mM | 750 mM | 625 mM | 500 mM | 500 mM | 400 mM | 300 mM |
| F | 25 mM | 25 mM | 25 mM | 25 mM | 25 mM | 25 mM | 750 mM | 625 mM | 500 mM | 500 mM | 400 mM | 300 mM |
| G | 50 mM | 100 mM | 200 mM | 50 mM | 100 mM | 200 mM | 1,250 mM | 1,750 mM | 2,500 mM | 600 mM | 800 mM | 1,000 mM |
| H | 50 mM | 100 mM | 200 mM | 50 mM | 100 mM | 200 mM | 1,250 mM | 1,750 mM | 2,500 mM | 600 mM | 800 mM | 1,000 mM |

TABLE 12

Arginine levels in each well

|   | 1 | 2 | 3 | 4 | 5 | 6 | 7 | 8 | 9 | 10 | 11 | 12 |
|---|---|---|---|---|---|---|---|---|---|---|---|---|
| A | 350 mM | 300 mM | 200 mM | 12 mM | 12 mM | 12 mM | 12 mM | 12 mM | 12 mM | 75 mM | 50 mM | 25 mM |
| B | 450 mM | 500 mM | 600 mM | 40 mM | 120 mM | 200 mM | 40 mM | 120 mM | 200 mM | 125 mM | 150 mM | 300 mM |
| C | 350 mM | 300 mM | 200 mM | 12 mM | 12 mM | 12 mM | 12 mM | 12 mM | 12 mM | 75 mM | 50 mM | 25 mM |
| D | 450 mM | 500 mM | 600 mM | 40 mM | 120 mM | 200 mM | 40 mM | 120 mM | 200 mM | 125 mM | 150 mM | 300 mM |
| E | 350 mM | 300 mM | 200 mM | 12 mM | 12 mM | 12 mM | 12 mM | 12 mM | 12 mM | 75 mM | 50 mM | 25 mM |
| F | 450 mM | 500 mM | 600 mM | 40 mM | 120 mM | 200 mM | 40 mM | 120 mM | 200 mM | 125 mM | 150 mM | 300 mM |
| G | 350 mM | 300 mM | 200 mM | 12 mM | 12 mM | 12 mM | 12 mM | 12 mM | 12 mM | 75 mM | 50 mM | 25 mM |
| H | 450 mM | 500 mM | 600 mM | 40 mM | 120 mM | 200 mM | 40 mM | 120 mM | 200 mM | 125 mM | 150 mM | 300 mM |

After the unique equilibration buffer was added to each well, a mixture of Myo-029 and aggregate was added to each well. The aggregate level in the load challenge was 25%. The buffer constituents were maintained at the same level as during equilibration. The material was shaken for 20 minutes, allowing equilibrium to be reached. The supernatant was removed from each well of the filterplate. Another stage of antibody preparation addition was made, and the plate shaken, and the supernatant removed. Up to seven stages were performed. The protein that had not bound in each stage was analyzed to determine overall protein concentration (by absorbance at A280 nm). The amount of monomer and aggregate was measured by size exclusion HPLC. Any decrease in aggregate indicated a condition conducive to purification. Tables 13 and 14 show the percentage of aggregate and monomer, by well, in a pool of the first four stages.

TABLE 13

Aggregate level (%)

|   | 1 | 2 | 3 | 4 | 5 | 6 | 7 | 8 | 9 | 10 | 11 | 12 |
|---|---|---|---|---|---|---|---|---|---|---|---|---|
| A | 8% | 6% | 3% | 4% | 7% | 16% | 3% | 3% | 3% | 5% | 3% | 3% |
| B | 12% | 15% | 17% | 3% | 3% | 5% | 3% | 4% | 4% | 6% | 5% | 5% |
| C | 7% | 6% | 3% | 4% | 4% | 3% | 5% | 4% | 4% | 6% | 6% | 4% |
| D | 13% | 14% | 14% | 6% | 4% | 7% | 5% | 6% | 4% | 8% | 8% | 7% |
| E | 11% | 10% | 6% | 4% | 19% | 11% | 5% | 6% | 7% | 9% | 8% | 6% |
| F | 15% | 19% | 20% | 4% | 3% | 10% | 6% | 8% | 10% | 10% | 10% | 17% |
| G | 10% | 9% | 6% | 6% | 3% | 7% | 8% | 14% | 17% | 10% | 16% | 22% |
| H | 16% | 18% | 20% | 4% | 5% | 17% | 9% | 15% | 17% | 12% | 17% | 18% |

TABLE 14

Monomer Recovery (%)

|   | 1 | 2 | 3 | 4 | 5 | 6 | 7 | 8 | 9 | 10 | 11 | 12 |
|---|---|---|---|---|---|---|---|---|---|---|---|---|
| A | 51% | 44% | 24% | 3% | 3% | 2% | 43% | 34% | 25% | 53% | 32% | 11% |
| B | 64% | 70% | 78% | 4% | 24% | 43% | 42% | 40% | 38% | 57% | 42% | 44% |
| C | 49% | 43% | 27% | 4% | 6% | 23% | 60% | 62% | 62% | 58% | 60% | 48% |
| D | 65% | 68% | 75% | 5% | 35% | 54% | 61% | 64% | 64% | 63% | 63% | 62% |
| E | 61% | 58% | 44% | 3% | 3% | 5% | 58% | 62% | 64% | 66% | 65% | 63% |
| F | 70% | 76% | 88% | 5% | 33% | 63% | 59% | 63% | 68% | 67% | 68% | 74% |
| G | 57% | 57% | 50% | 4% | 7% | 65% | 72% | 82% | 85% | 70% | 80% | 83% |
| H | 71% | 75% | 85% | 5% | 48% | 75% | 69% | 82% | 88% | 71% | 80% | 87% |

The high throughput screen was able to qualitatively predict the monomer recovery and HMWA removal in a column purification scheme. For instance, the conditions from well C8 (20 mM HEPES, 1 mM Phosphate, 1750 mM NaCl, and 12 mM arginine, pH 7.2) were tested on a column packed with cHA Type I resin. Aggregate levels were reduced to 2.5% and the monomer yield was 72%, after column purification. The conditions from well D5 (20 mM HEPES, 5 mM Phosphate, 100 mM NaCl, and 120 mM arginine, pH 7.2) were also tested on a column packed with cHA-1 resin. Aggregate levels were reduced to 0.7% and the monomer yield was 73%, after column purification. Finally, the conditions equivalent to well C3 (100 mM HEPES, 1 mM Phosphate, 120 mM NaCl, and 200 mM arginine, pH 7.2, where the high level of HEPES contributes ionic strength similarly to the NaCl) were tested on a column packed with cHA-1 resin. Aggregate levels were reduced to 4%, with a monomer recovery of 69%, after column purification. These results demonstrate that high throughput screening underestimates column performance as measured by both monomer recovery and HMWA removal. However, high throughput screening is able to qualitatively predict both yield and purity.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

We claim:

1. A method for purifying at least one antibody monomer from an antibody preparation containing high molecular weight aggregates (HMWA) comprising:
    contacting a hydroxyapatite resin with the antibody preparation in load buffer comprising from 1 to 20 mM sodium phosphate and from 0.2 to 2.5 M NaCl, allowing the purified antibody to flow through the column, while impurity HMWA binds to the column.

2. The method of claim 1, wherein the purified antibody contains less than 5% high molecular weight aggregates.

3. The method of claim 1, wherein the purified antibody contains less than 1% high molecular weight aggregates.

4. The method of claim 1, wherein the load buffer has a pH from 6.4 to 7.6.

5. The method of claim 4, wherein the load buffer contains 3 mM or 5 mM sodium phosphate.

6. The method of claim 4, wherein the load buffer contains 1 M or 0.35 M NaCl.

7. The method of claim 4, wherein the load buffer has a pH of 6.8 or 7.2.

8. The method of claim 1, wherein the antibody is an IgG, IgA, IgD, IgE, or IgM antibody.

9. The method of claim 1, wherein the antibody is monoclonal, polyclonal, chimeric, humanized, or a fragment thereof.

10. The method of claim 1, wherein the antibody is an anti-IL-21 receptor, anti-GDF-8, anti-Abeta, anti-CD22, anti-Lewis Y, anti-IL-13, or anti-IL-22 antibody.

11. The method of claim 1, wherein the antibody has a basic pI.

12. The method of claim 1, wherein the resin is ceramic hydroxyapatite type I or type II.

13. The method of claim 12, wherein the resin is ceramic hydroxyapatite type I.

14. The method of claim 1, wherein the purified antibody contains less than 300 ppm Protein A.

15. A method for purifying at least one antibody monomer from an antibody preparation containing high molecular weight aggregates (HMWA) comprising subjecting the antibody preparation to
    (a) Protein A affinity chromatography,
    (b) ion exchange chromatography,
    (c) hydroxyapatite chromatography, and
    (d) contacting the hydroxyapatite chromatography comprising a hydroxyapatite resin with the antibody preparation in load buffer comprising from 1 to 20 mM sodium phosphate and from 0.2 to 2.5 M NaCl, allowing the purified antibody to flow through the resin, while impurity HMWA binds to the resin.

16. The method of claim 15, wherein the Protein A affinity chromatography is performed first and the hydroxyapatite chromatography is performed last.

17. The method of claim 15, wherein the ion exchange chromatography is anion exchange chromatography.

18. A method for purifying at least one antibody monomer from an antibody preparation containing high molecular weight aggregates (HMWA) comprising:
    (a) contacting the preparation with a Protein A support;
    (b) allowing the antibody to adsorb to the Protein A support;
    (c) washing the Protein A support and adsorbed antibody with at least one Protein A washing buffer;
    (d) eluting the adsorbed antibody with at least one Protein A elution buffer;
    (e) contacting the Protein A eluate with an ion exchange support;
    (f) allowing the antibody to flow through the ion exchange support, while impurity HMWA binds to the ion exchange support;
    (g) washing the ion exchange support with at least one ion exchange washing buffer;
    (h) exchanging the ion exchange flow-through into a load buffer comprising from 1 to 20 mM sodium phosphate and from 0.2 to 2.5 M NaCl;
    (i) contacting the ion exchange flow-through with a hydroxyapatite resin;
    (j) allowing the antibody to flow through the hydroxyapatite resin; and
    (k) washing the hydroxyapatite resin with at least one hydroxyapatite washing buffer.

19. The method of claim 18, wherein the ion exchange chromatography is anion exchange chromatography.

20. The method of claim 18, further comprising filtering the ion exchange flow-through before application to the hydroxyapatite resin, thereby reducing the viral contaminants.

21. The method of claim 18, further comprising subjecting the hydroxyapatite eluate to at least one of ultrafiltration or diafiltration.

* * * * *